US008667715B2

(12) United States Patent
Santopietro et al.

(10) Patent No.: US 8,667,715 B2
(45) Date of Patent: Mar. 11, 2014

(54) ORTHOTIC DEVICES AND METHODS FOR MANUFACTURING SAME

(75) Inventors: Frank J. Santopietro, Brookline, MA (US); David R. Santopietro, Jamaica Plain, MA (US)

(73) Assignee: Santtro, LLC, Brookline, MA (US)

( * ) Notice: Subject to any disclaimer, the term of this patent is extended or adjusted under 35 U.S.C. 154(b) by 0 days.

(21) Appl. No.: 12/900,365

(22) Filed: Oct. 7, 2010

(65) Prior Publication Data

US 2011/0083345 A1    Apr. 14, 2011

Related U.S. Application Data

(60) Provisional application No. 61/278,719, filed on Oct. 9, 2009.

(51) Int. Cl.
*A43B 7/14* (2006.01)
*A43B 7/22* (2006.01)
*A43B 13/00* (2006.01)
*A61F 5/14* (2006.01)

(52) U.S. Cl.
USPC ..................................... 36/140; 36/43; 36/180

(58) Field of Classification Search
USPC .................. 36/71, 43–44, 140, 142–145, 154, 36/180–181
See application file for complete search history.

(56) References Cited

U.S. PATENT DOCUMENTS

| 4,180,924 A | 1/1980 | Subotnick |
| 4,266,553 A | 5/1981 | Faiella |
| 4,517,981 A | 5/1985 | Santopietro et al. |
| 4,627,177 A * | 12/1986 | Meyers .............................. 36/43 |
| 4,642,911 A * | 2/1987 | Talarico, II .................... 36/30 R |
| 4,769,926 A * | 9/1988 | Meyers .............................. 36/43 |

(Continued)

FOREIGN PATENT DOCUMENTS

| DE | 1 932 141 | 3/1996 |
| EP | 1 652 440 A1 | 3/2006 |
| WO | WO 01/49143 A1 | 7/2001 |

OTHER PUBLICATIONS

International Search Report and Written Opinion of the International Search Authority mailed Jan. 19, 2012 for International Application No. PCT/US2010/051851 filed Oct. 7, 2010.

(Continued)

*Primary Examiner* — Jila M Mohandesi
*Assistant Examiner* — Tiffany Drake
(74) *Attorney, Agent, or Firm* — Hamilton, Brook, Smith & Reynolds, P.C.

(57) ABSTRACT

Embodiments of the present invention relate to an orthotic device used for controlling motion of a human foot in a functionally corrected anatomical position from heel strike through toe off. The orthotic device may include at least one of rearfoot, midfoot, forefoot, and toe regions. In each region corresponding medial and lateral wedges may be employed. In the rearfoot region, the medial and lateral wedges intersect at an expected contact location of a medial side of a midline of a heel of the human foot. In the midfoot region, the medial and lateral wedges intersect inclusively between expected contact locations of a first cuneiform bone and a cuboid bone. In the forefoot region, the medial and lateral wedges intersect inclusively between expected contact locations of first and fifth metatarsal bones. In the toe region, the medial and lateral wedges intersect inclusively between expected contact locations of first and fifth toes.

13 Claims, 15 Drawing Sheets

(56) References Cited

U.S. PATENT DOCUMENTS

| | | | |
|---|---|---|---|
| 4,905,383 A * | 3/1990 | Beckett et al. | 36/28 |
| 5,014,706 A * | 5/1991 | Philipp | 36/140 |
| 5,212,894 A * | 5/1993 | Paparo | 36/43 |
| 5,509,218 A * | 4/1996 | Arcan et al. | 36/43 |
| 6,092,314 A | 7/2000 | Rothbart | |
| 6,212,723 B1 * | 4/2001 | Rothbart | 12/133 R |
| 6,725,578 B2 * | 4/2004 | Kerrigan | 36/144 |
| 6,920,705 B2 * | 7/2005 | Lucas et al. | 36/25 R |
| 7,191,552 B1 * | 3/2007 | Husom | 36/144 |
| 7,484,319 B2 * | 2/2009 | Cheskin et al. | 36/44 |
| 2006/0059726 A1 * | 3/2006 | Song et al. | 36/142 |
| 2006/0242860 A1 * | 11/2006 | Canvin | 36/83 |
| 2009/0313858 A1 * | 12/2009 | Andriacchi et al. | 36/140 |

OTHER PUBLICATIONS

Santopietro Frank J., "Foot and foot-related injuries in the young athlete", *Clin Sports Med* 7:563-89 (1998).

Notification Concerning Transmittal of International Preliminary Report on Patentability and International Preliminary Report on Patentability in International Application No. PCT/US2010/051851, 8 pages, mailed Apr. 11, 2012.

* cited by examiner

Pronation

Supination

Pronation

ORTHOTIC DEVICES AND METHODS FOR MANUFACTURING SAME

RELATED APPLICATION

This application claims the benefit of U.S. Provisional Application No. 61/278,719, filed on Oct. 9, 2009. The entire teachings of the above application are incorporated herein by reference.

BACKGROUND

As explained in U.S. Pat. No. 4,517,981, the teachings of which are incorporated herein by reference in its entirety, each joint of the human foot has a specific function and covers a certain range of motion. Human feet may be categorized into various types (i.e., structures and shapes). A human foot type effects the impact endured by a foot during heel strike (e.g., while walking, jogging, or running). A human foot type may be determined based on the shape of the foot, the shape of the arch of the foot, and the extent of rotational movement of the foot (i.e., pronation).

A neutrally functioning foot ideally contacts the ground in a slightly supinated or high-arched position and pronates (i.e., flattens out) to conform to the ground. In contrast, some neutral, flat and high-arched feet may already be pronated (i.e., flat) at heel strike (or foot contact) and, as such, cannot conform to the ground (decelerate) and absorb shock.

In a high-arched foot, the first metatarsal bone is generally lower than the other metatarsal bones, in relation to the plane of the rearfoot or undersurface of the heel. This condition is commonly referred to as a plantar-flexed first metatarsal.

In a flat foot, the first metatarsal bone is usually elevated in relation to the plane of the rearfoot or undersurface of the heel. The first metatarsal bone may be in the same plane as the remaining metatarsal bones or at higher or lower planes. The first metatarsal bone in a flat foot can be very flexible and can bend easily when weight is placed on the foot to allow the rearfoot to flatten out or pronate with no resistance.

Standing extended periods of time or walking long distances can be uncomfortable if the feet are not in functionally corrected positions. Many of today's footwear, even walking and running shoes and orthotic inserts, can attempt to address high-arched or flat feet, but without addressing other interrelated issues in the very complex bone, ligaments, and muscle structures in the feet and lower extremities, these attempts can be ineffective at best or exacerbate otherwise subtle discomforts at worst.

SUMMARY

An example embodiment of the present invention relates to a method and corresponding orthotic device (or shoe) for dynamically controlling the motion of a human foot in a functionally corrected anatomical position from heel strike through toe off. The orthotic device includes a rearfoot region that includes rearfoot medial and lateral wedges. The rearfoot medial and lateral wedges intersect at an expected contact location of a medial side of a midline of a heel of the human foot on the rearfoot region of the orthotic device. The orthotic device further includes a midfoot region that includes midfoot medial and lateral wedges. The midfoot medial and lateral wedges intersect inclusively between expected contact locations of a first cuneiform bone and a cuboid bone on the midfoot region of the orthotic device. The orthotic device also includes forefoot region that includes forefoot medial and lateral wedges. The forefoot medial and lateral wedges intersect inclusively between expected contact locations of first and fifth metatarsal bones on the forefoot region of the orthotic device. The orthotic device further includes a toe region that includes toe medial and lateral wedges. The toe medial and lateral wedges intersect inclusively between expected contact locations of first and fifth toes on the toe region of the orthotic device.

Another example embodiment of the present invention relates to a method and corresponding orthotic device for dynamically controlling the motion of a human foot in a functionally corrected anatomical position. The orthotic device includes a medial wedge, a lateral wedge, and an intersection defined where the medial and lateral wedges intersect. The intersection extends from a medial side of a midline of a heel of the human foot to, and inclusively between, expected contact locations of first and fifth toes of the foot on the orthotic device. The medial wedge, lateral wedge, and intersection are configured to dynamically control the motion of the human foot in functionally corrected anatomical position from heel strike through toe off.

Another example embodiment of the present invention relates to a method and corresponding orthotic device for dynamically controlling the motion of a human foot in a functionally corrected anatomical position. The orthotic device includes a medial wedge, a lateral wedge, and a support. The support is defined by a contour of the medial wedge, extending from an intersection of the medial wedge and lateral wedge at an expected contact location of a second metatarsal head and neck area. The support projects inclusively between fore and aft joints of a first metatarsal bone, and optionally slightly beyond, such as a toe's width, at an angle determined as a function of a degree of plantar-flexion of the first metatarsal bone. The angle is referred to as plantar flexion angle (interchangeably referred herein as a cutback angle) and is defined as a function of a difference between angles in a z-direction of first and fifth and second and fifth metatarsal heads.

A further example embodiment of the present invention relates to a method and corresponding orthotic device for dynamically controlling the motion of a human foot. The orthotic device includes a forefoot structure having a forefoot angle, a rearfoot structure having a rearfoot angle, and a lateral flange having a width, depth, and length. The width, depth, and length of the lateral flange are a function of the forefoot angle, rearfoot angle, or combination thereof.

Another example embodiment of the present invention relates to a method and corresponding apparatus that determines a prescription for an orthotic device. The example embodiment obtains measurements of width and length of a human foot and determines locations of metatarsal heads of the human foot. The example embodiment determines the prescription for an orthotic device, including a toe wedge, first metatarsal plantar flexion angle-based support, or lateral flange, the prescription being a function of the measurements and locations of the metatarsal heads.

Yet another example embodiment of the present invention relates to a method and corresponding apparatus that provides a person with an orthotic device. The example embodiment obtains a desired footwear from the person and selects an orthotic device configured to be used with the desired footwear, where the orthotic device includes a toe wedge, plantar flexion angle-based support, or lateral flange according to a prescription specified to arrange metatarsal heads of the person's feet in a functionally corrected anatomical position from heel strike through toe off. The example embodiment provides a report of the orthotic device selected to be used in shoes having the footwear obtained from the person.

Another example embodiment of the present invention relates to a method and corresponding apparatus that generates codes to enable a computer numerically controlled (CNC) machine to produce an orthotic device. The example embodiment obtains a measurement of length of a human foot, measurements of width of the foot at a forefoot and heel, and locations of metatarsal heads relative to the length and widths. The example embodiment determines the prescription for the orthotic device having a toe wedge, a plantar flexion angle-based support, or lateral flange as a function of the length and width measurements and metatarsal head locations. The example embodiment generates codes to provide to a CNC machine to enable the CNC machine to produce the orthotic device from raw material according to the prescription to provide the person with the orthotic device.

Yet another example embodiment of the present invention relates to a method and corresponding apparatus that transforms footwear to functionally correct the anatomical position of a wearer's foot from heel strike to toe off. The example embodiment obtains the footwear and employs the device in the footwear. The device includes a toe wedge, plantar flexion angle-based support, or lateral flange.

Another example embodiment of the present invention relates to a multi-level orthotic device kit for dynamically controlling the motion of a person's foot. The multi-level orthotic device kit includes a plurality of orthotic devices including a first level orthotic device and a final level orthotic device, optionally with at least one intermediate level orthotic device. The plurality of orthotic devices are included to facilitate transitioning the human foot from wearing the first level orthotic device to the final level orthotic device over a given length of time. In one embodiment, the final level orthotic device has angles defined thereby that apply substantially different forces on a foot during walking than during walking without the final level orthotic device such that using the final orthotic device is uncomfortable without graduating up to it via using the first (and possible other) orthotic devices. The final level orthotic device corresponds to a prescription for the person and for controlling the person's foot in a functionally corrected anatomical position as a function of applying at least one of a toe wedge, a plantar flexion angle-based support, or a lateral flange.

Yet another example embodiment of the present invention relates to a method for distributing an orthotic device kit. The example embodiment assembles a plurality of orthotic devices including a first level orthotic device and a final level orthotic device. The orthotic devices are included to facilitate transitioning the human foot from wearing the first level orthotic device to the final level orthotic device over a given length of time. The final level orthotic device corresponds to a prescription for the person and for controlling the person's foot in a functionally corrected anatomical position as a function of applying at least one of a toe wedge, a plantar flexion angle-based support, or a lateral flange. The example embodiment packs the plurality of orthotic devices into an orthotic device kit and distributes the orthotic device kit to retail entities.

In the view of the foregoing, the following description illustrates example embodiments and features that may be incorporated into an orthotic device, where the term "orthotic device" may be interpreted as an orthotic device, a subsystem of an orthotic device, apparatus, method or any combination thereof, with regard to embodiments of the present invention.

The orthotic device may include at least one medial wedge that has a larger angle than its corresponding lateral wedge. The orthotic device may include at least one medial wedge that has a smaller angle than its corresponding lateral wedge. The medial wedges in the rearfoot, midfoot, and forefoot regions may have larger angles than their respective lateral wedges, and the at least one medial wedge in the toe region may have a smaller angle than its corresponding lateral wedge. The at least one pair of medial and lateral wedges may increase or decrease toward their respective intersections. The medial wedge may be defined by an angle greater or less than the lateral wedge in at least a portion of the orthotic device. The medial and lateral wedges may have corresponding edges distal from the intersection, and the wedges may increase or decrease in height from their edges toward the intersection. The medial wedge angle may be greater or less than an angle defining the lateral wedge.

The orthotic device may further include a heel-to-toe wedge. The heel-to-toe wedge may increase or decrease from the rearfoot region to the forefoot region.

The plantar flexion angle may be arranged to cause the first metatarsal bone to be in a correct anatomical orientation in relation to second, third, fourth, and fifth metatarsal bones.

The forefoot structure may include at least one of a toe wedge or a forefoot wedge. The rearfoot structure may include at least one of a midfoot wedge or a rearfoot wedge.

The orthotic device may include a medial flange having a width defined as a function of the width relationship of the lateral flange. An increase in width of the forefoot structure or the rearfoot structure may result in an increase in the width and depth of the lateral flange. An increase in width of the forefoot structure or the rearfoot structure may result in an increase in the depth of the lateral flange.

The measurements used in determining a prescription may be biomechanical measurements including measurement of angles and joints.

In order to produce an orthotic device, a computer numerical controlled machine (CNC) may be provided with the prescription in a form of computer numerically controlled codes. The CNC machine may include a machine tool configured to be applied to a bottom or top portion of raw orthotic material. The machine tool may mill the raw orthotic along a vertical axis of the raw orthotic from vertical or horizontal directions.

The transformation of a shoe may include obtaining the shoe by constructing, manufacturing, or reprocessing of the shoe, and employing the insole may include shaping a sole of the shoe to accommodate the insole.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION

A description of example embodiments follows.

Figure 1:
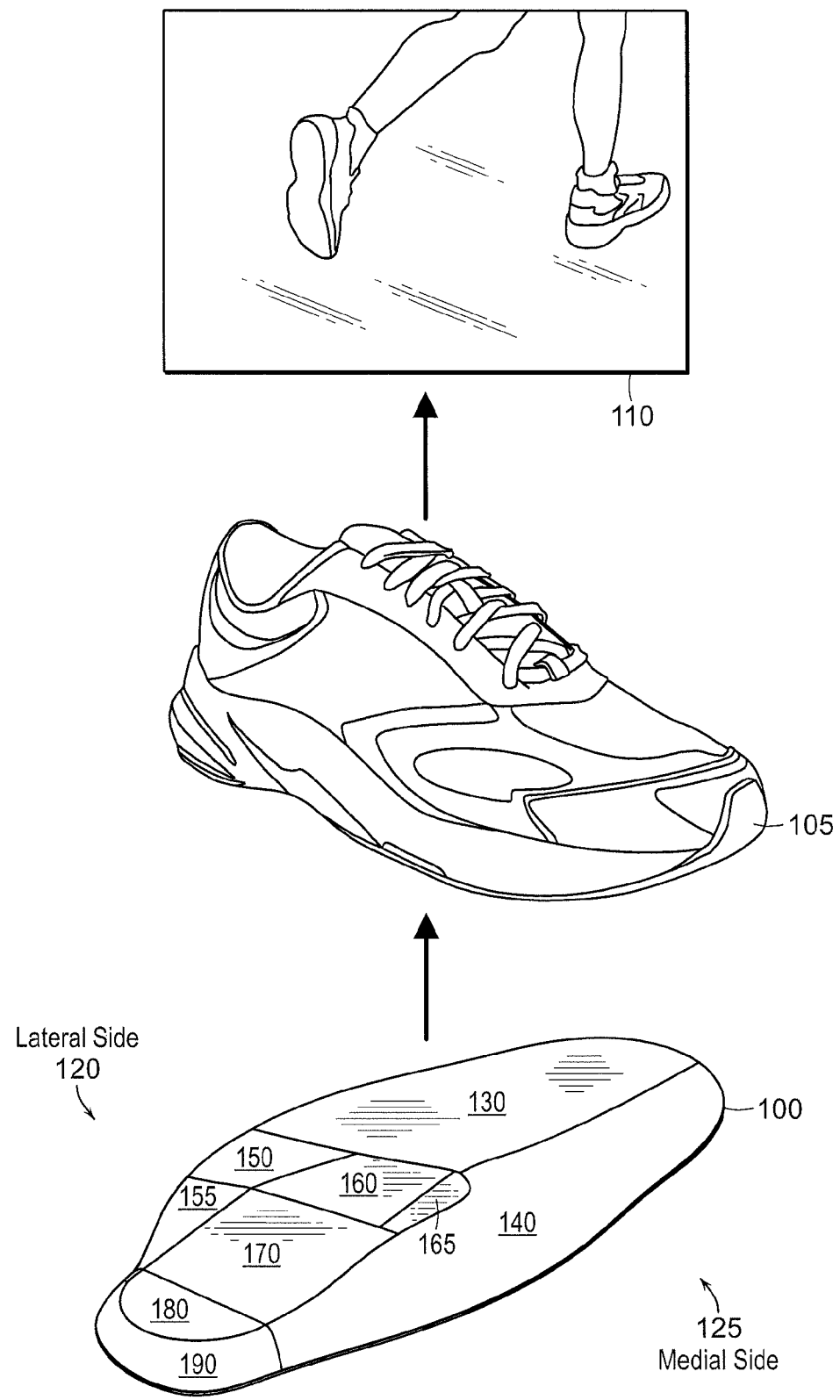
FIG. 1 is a diagram of an example embodiment of the present invention.

FIG. 1 is a high level illustration of an example orthotic device 100 according to embodiments of the present invention. The orthotic device 100 is designed to provide added functionality and comfort to a human foot. Specifically, the orthotic device 100 positions the foot in a supinated position at heel strike (i.e., heel contact). The orthotic device 100 allows for the foot to continue to decelerate slowly after making heel strike (i.e., pronate slowly). The orthotic device 100 further allows for the foot to continue decelerating at up to 25% of the stance phase of gait coinciding with the point at which pelvis and thigh of the contact limb externally rotate. The foot and the leg are either completely in sync with the axis of rotation of thigh and pelvis or they may lag behind.

The orthotic device 100 is arranged to ensure that the external rotation of the thigh and pelvis are accompanied by foot supination (i.e., acceleration) and that the internal rotation of the thigh and pelvis are accompanied by foot pronation (i.e., deceleration). Specifically, the orthotic device 100 is arranged to employ a wedge, which may, in turn, include a plurality of wedges, to slow down and encourage pronation. The multiple wedges employed in the orthotic device 100 may cover the heel area (heel wedge 190 and rear foot wedge 180) and continue to maintain the foot through the midfoot and forefoot (wedges labeled as 150, 155, 160, 165, 170) into the toe area (wedges labeled 130, 140).

The orthotic device 100 can be described in terms of a medial side 125 and a lateral side 120. Wedges on the medial side 125 may be referred to herein as medial wedges, and wedges on the lateral side 120 may be referred to as lateral wedges. Together, medial and lateral wedges help stabilize the foot medially and laterally from heel contact through toe off. It should be understood that wedges may have more than one label depending on which regions of the foot the wedges support. Further, although defined as wedges, the wedges 130-190 of the orthotic device 100 may have one or multiple slopes, and zero, positive, or negative slopes are possible for any of the wedges.

An orthotic device 100 according to example embodiments of the present invention may be employed as an insole in a shoe 105 worn by a patient 110. In certain embodiments, a shoe 105 may be manufactured or reprocessed to include the orthotic device 100 or portions of the orthotic device 100 (e.g., wedges labeled 130-190 in FIG. 1).

The shoe manufactured, modified, or supplemented to include the orthotic device 100 may be any type of shoe, including sneakers, tennis shoes, flats, heels, etc. The term "shoe" herein is used to generally refer to any kind of footwear or component thereof. Certain embodiments may only include a portion of the wedges illustrated. For example, certain embodiments may be limited to the use of heel 190 and rearfoot 180 wedges.

Example embodiments may be used to dynamically control the motion of a human foot in a functionally corrected anatomical position. Example embodiments may be utilized in one shoe only (i.e., right or left shoe) or in both shoes.

Figure 2A:
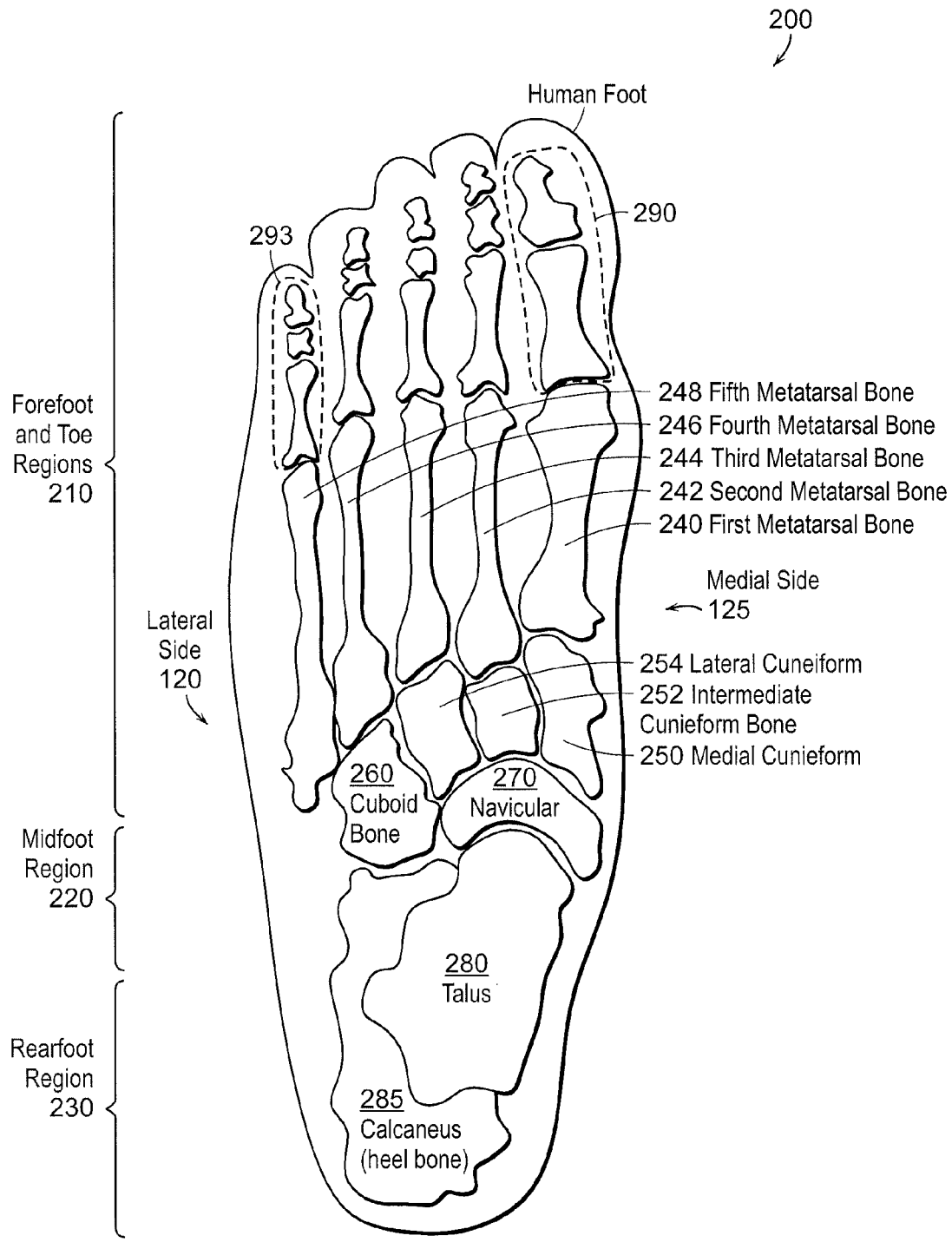
FIG. 2A is a structural diagram of a human foot.

FIG. 2A is a high level illustration of a human foot 200. As shown in FIG. 2, the human foot includes a lateral side 120 and a medial side 125. Example embodiments of the present invention view a human foot as having the following regions:

Forefoot and toe regions 210 including toe, sesamoid, and metatarsal bones. The five toes are commonly referenced with numbers 1 though 5 and include a first toe 290 (commonly known as the big toe) and the fifth toe 293. The metatarsal bones are also commonly referenced with numbers and include first 240, second 242, third 244, fourth 246, and fifth 248 metatarsal bones.

Midfoot region 220 includes cuboid 260, navicular 270, and cuneiform bones. The cuneiform bones include medial 250, intermediate 252, and lateral 254 cuneiform bones.

The rearfoot region 230 includes the talus bone 280 and calcaneus bone 285 (commonly referred to as the heel bone).

The bone structure of the human foot 200 is provided for purposes of providing a high level reference for understanding the example embodiments provided herein.

The human foot absorbs shock, acts as a rigid lever for propulsion, and helps with transferring the weight of the human body forward. These functions are achieved mainly through subtalar joint and midtarsal joint motions (not shown).

Figure 2B:
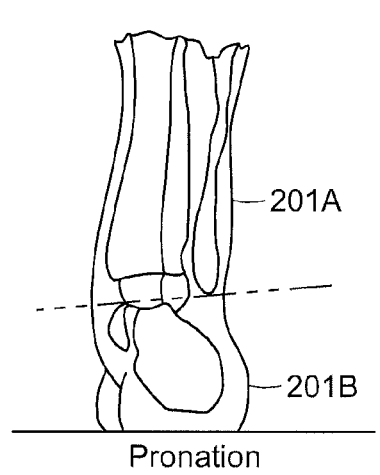
FIG. 2B illustrates a high level diagram of pronation in a human foot.

FIG. 2B illustrates a high level diagram 201 of pronation in a human foot. Pronation in the subtalar joint is the rotational movement of this joint and can be described as motion in eversion, abduction, and dorsiflexion.

Figure 2C:
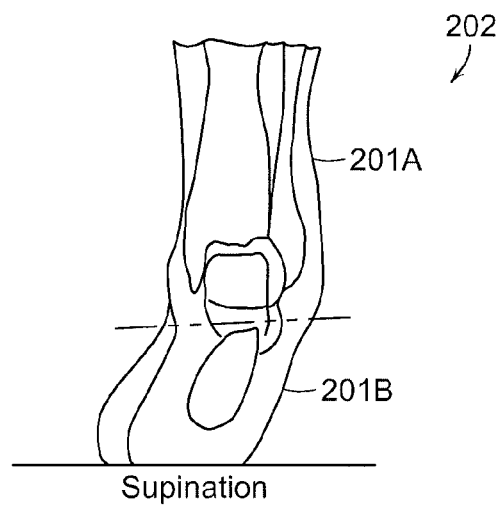
FIG. 2C illustrates a high level diagram of supination in a human foot.

FIG. 2C illustrates a high level diagram 202 of supination in a human foot. Supination of the subtalar joint is the opposite of pronation and is described as inversion, adduction, and plantarflexion. This motion may take place in weight bearing (also referred to as closed chain motion) or non-weight bearing (also referred to as opened chain motion). In a closed chain motion, the leg segment 201a of is moving over the stationary foot segment 201b. In open chain motion, the foot segment 201b is moving around leg segment 201a.

Figure 2D:
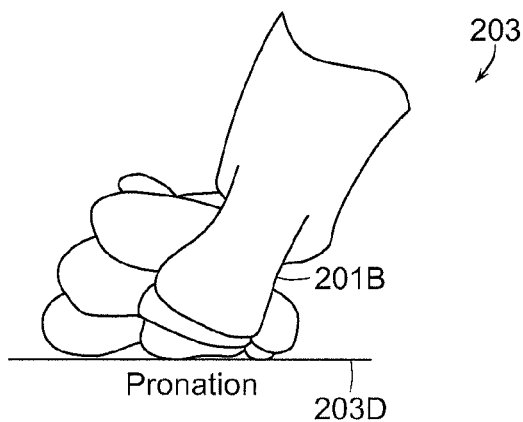
FIG. 2D is a high level illustration of pronation at foot contact.

FIG. 2D is a high level illustration 203 of pronation at foot contact. In a neutral gait progression, the foot makes contact with the ground 203d in a slightly supinated position. Therefore, at foot contact (or heel contact), the heel 201b is slightly inverted. Upon making the contact, the heel 201b undergoes pronation. This pronation is initiated by the reactive force of the ground which results in directing the lateral side of the foot into pronation. The medial side of the foot is also forced downward. The combination of these motions helps the foot adapt or make contact with the ground.

Figure 2E:
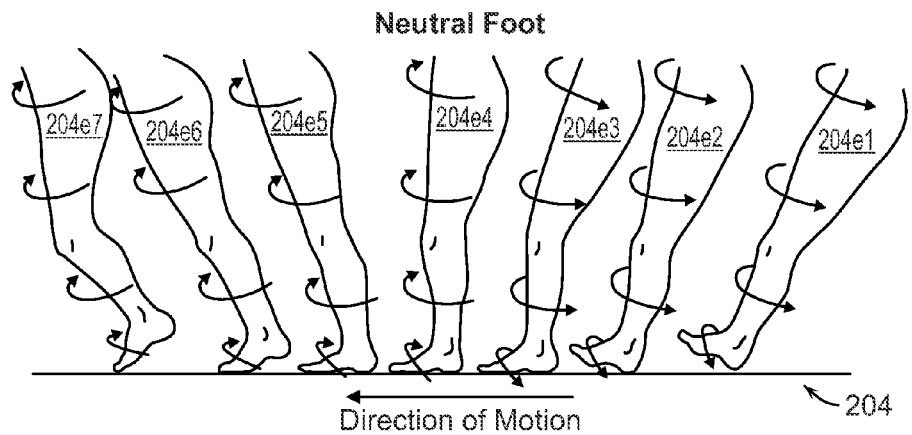
FIG. 2E is a high level illustration of pronation of a leg with a neutral foot.

FIG. 2E is a high level illustration 204 of rotation of a leg and pronation of a foot with a neutral foot making contact with the ground during the gait cycle. The heel contacts the ground 204e1 with the foot at slightly supinated position. The foot then pronates while the leg is internally rotating along with the thigh and pelvis. The foot continues to pronate and the leg, thigh, and pelvis continue to internally rotate 204e2. When the pelvis is maximally internally rotated along with the thigh and leg, the foot is maximally pronated and the leg should be perpendicular to the ground 204e3. The pelvis then begins to externally rotate along with the thigh and leg, and the foot begins to supinate 204e4. These motions continue throughout the rest of the gait cycle 204e5-204e7.

Figure 2F:
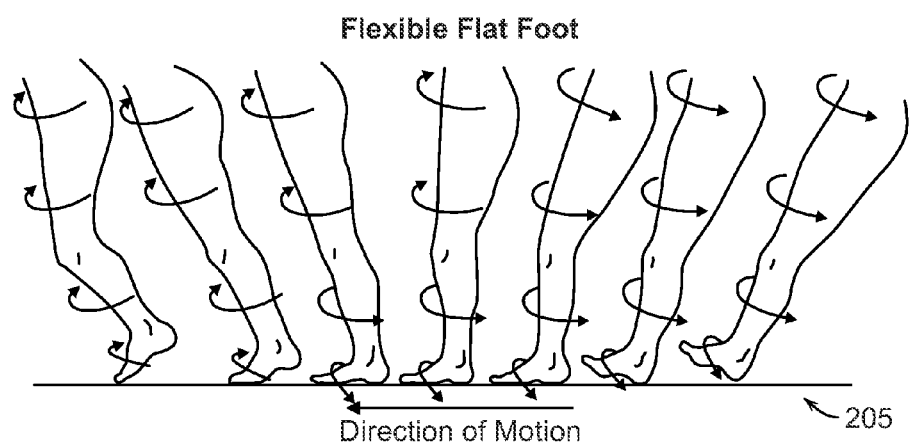
FIG. 2F is a high level illustration of pronation of a leg with a flat foot.

FIG. 2F is a high level illustration 205 of a lower extremity with a flexible flat foot making contact with the ground during the gait cycle. The foot of a person suffering from a flexible flat foot may be slightly supinated but pronates more (hyperpronate) than that of a person having a neutral foot (shown in FIG. 2E) and the pronation continues beyond midstance or when the pelvis begins to externally rotate. The foot stays pronated along with the leg but the thigh generally externally rotates along with the pelvis. This creates an unsynchronized juncture at the knee joint and can lead to excessive stress created in the feet and lower legs. This excessive and prolonged pronation and delayed supination are responsible for many pediatric and adult foot problems.

Figure 2G:
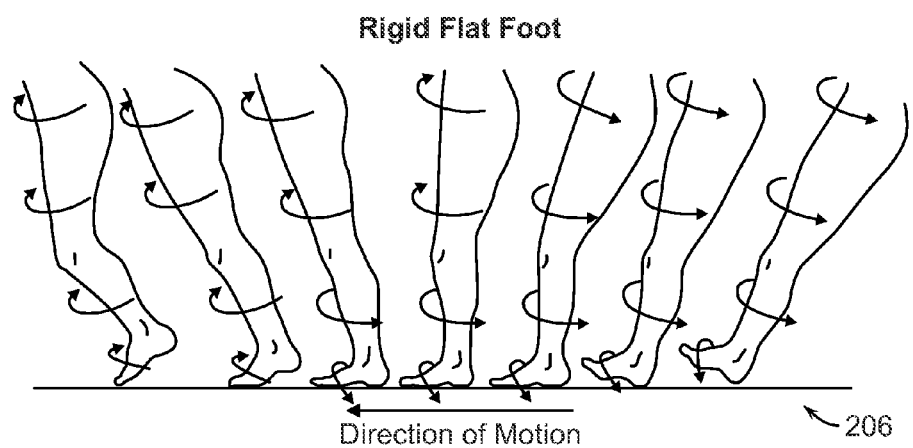
FIG. 2G is a high level illustration of a lower extremity with a rigid flat foot making contact with the ground during the gait cycle.

FIG. 2G is a high level illustration 206 of a lower extremity with a rigid flat foot making contact with the ground during the gait cycle. The foot of a person with a rigid flat foot hits the ground in a pronated position. Since the foot is maximally pronated, there is no deceleration after foot contact and, therefore, no shock absorption resulting in a hard or violent heel/foot strike. After foot or heel contact, the foot and leg remain pronated and internally rotated beyond midstance. The pelvis begins to externally rotate at midstance (25% of stance phase of gait) in spite of the fact that the foot and leg are pronated and internally rotated. The thigh moves externally with the pelvis and creates a torsional stress at the knee joint. The foot remains pronated or internally rotated until the heel comes off the ground. The forefoot is then forced into external rotation by the motion of the pelvis moving externally. This external motion can be severe and result in considerable foot and leg pathology. This foot hits the ground flat and stays flat throughout the stance phase and through the swing phase of gait.

Regardless of whether pronation or supination are present, sufficient or excessive, as the body moves forward, the internal and external pelvic motions drive the movement of the body. However, the insufficiency of pronation or supination may result in torsional stress. This torsional stress may be relieved at the foot to ground interface, at the foot to shoe interface, at the shoe to ground interface, or possibly in more proximal areas, such as the knee and hip joint. Orthotic devices, such as those presented in relation with example embodiments of the present invention, may be used to control and/or alter biomechanics of the foot and provide relief to patients suffering from a vast range of foot, leg, and back problems, such as those described above.

Figure 3:
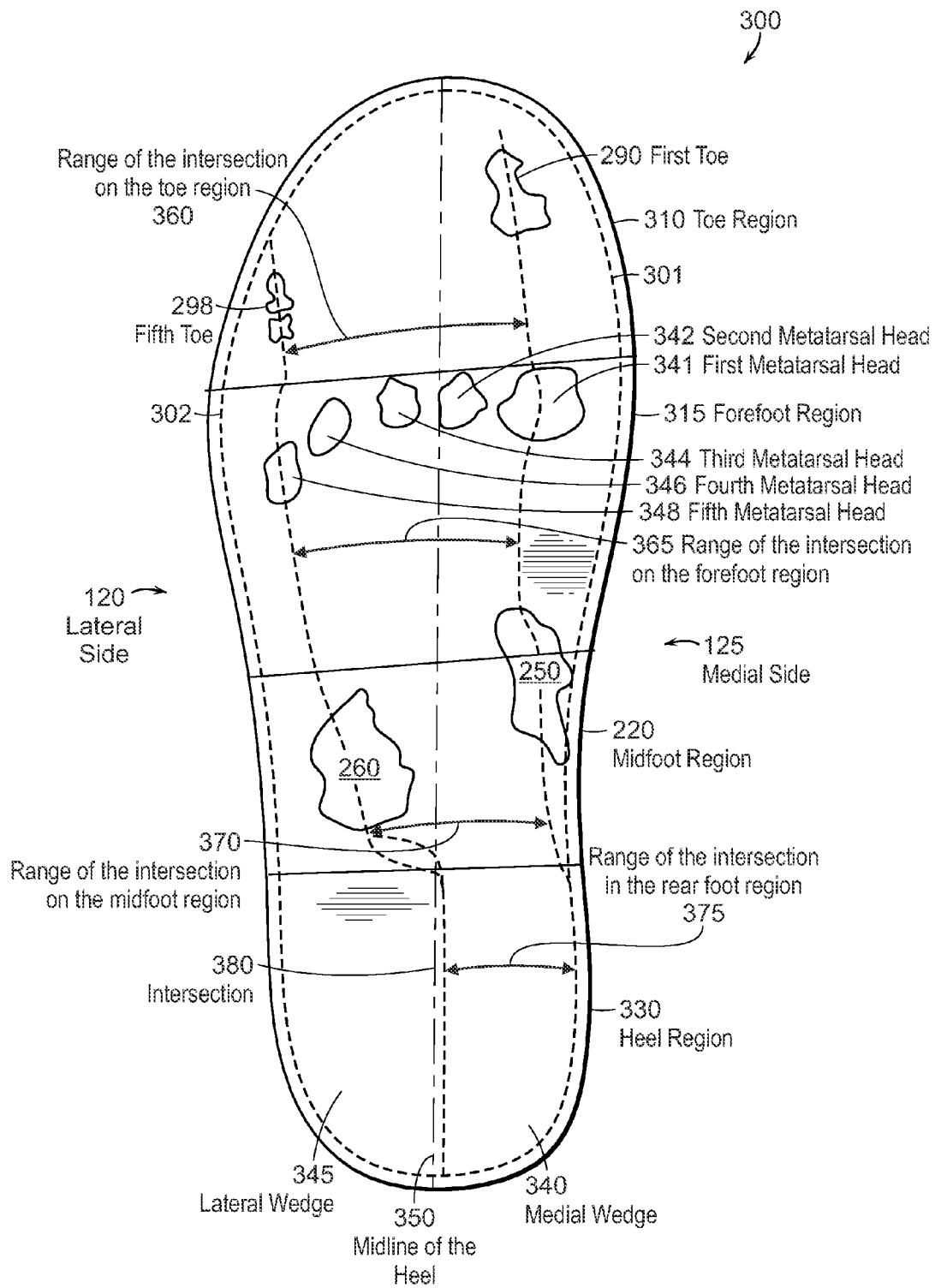
FIG. 3 is an correspondence diagram of an example embodiment of the present invention in connection with a human foot.
Figure 4:
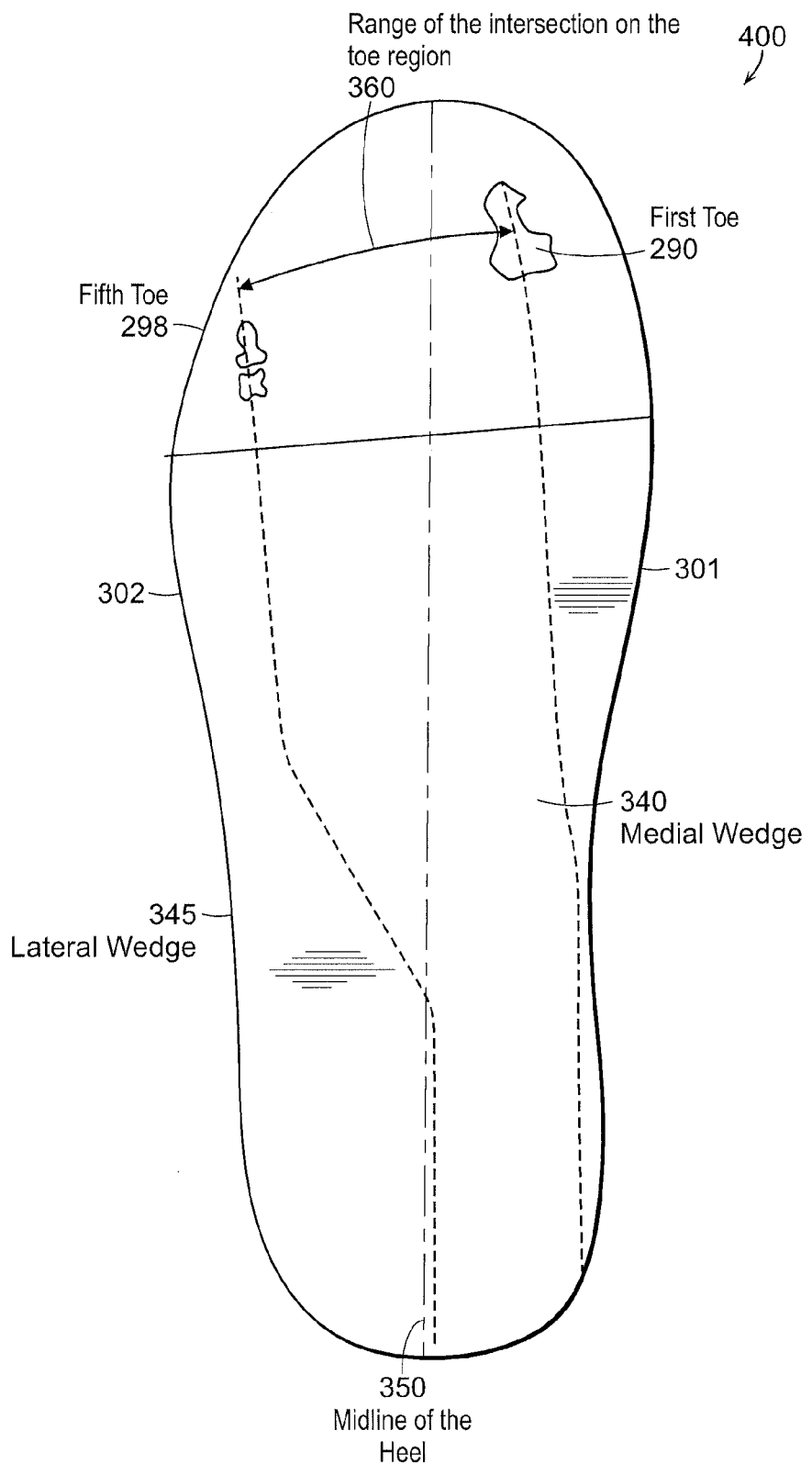
FIG. 4 is another correspondence diagram of an example embodiment of the present invention, including medial and lateral wedges, in connection with a human foot.

FIG. 3 is an illustration of an example of an orthotic device 300 according to embodiments of the present invention. FIG. 4 is another diagram of an example of an orthotic device 400 according to an embodiment of the present invention, including medial and lateral wedges, in connection with a human foot. The orthotic device 300 includes a toe region 310, forefoot region 315, midfoot region 220, and heel region 330. The head and neck regions of the metatarsal bones are referred to herein after as "metatarsal heads." These regions are shown as first 341, second 342, third 344, fourth 346, and fifth 348 metatarsal heads. Dashed lines 301 and 302 denote the insole line of the orthotic device 300.

The toe region 310 includes toe medial 340 and lateral 345 wedges that intersect, inclusively, between expected contact locations of first 290 and fifth 298 toes on the toe region 310 of the orthotic device 300. Therefore, the toe medial 340 and lateral 345 wedges may intersect inclusively between and under first 290 and fifth 298 toes. An expected range arrow 360 indicates possible intersection of the medial 340 and lateral 345 wedges in the toe region 310.

The forefoot region 315 includes forefoot medial 340 and lateral 345 wedges that intersect, inclusively, between expected contact locations of first 341 and fifth 348 metatarsal heads on the forefoot region 315 of the orthotic device 300. Therefore, the forefoot medial 340 and lateral 345 wedges may intersect inclusively between first 341 and fifth 348 metatarsal heads. An expected range arrow 365 indicates a range of possible intersections of the medial 340 and lateral 345 wedges in the forefoot region 315.

The midfoot region 220 includes medial 340 and lateral 345 wedges that intersect, inclusively, between expected contact locations of the first cuneiform bone 250 (i.e., medial cuneiform bone 250) and the cuboid bone 260 on the midfoot region 220 of the orthotic device 300. An expected range arrow 370 indicates a range of possible intersections of the medial 340 and lateral 345 wedges in the midfoot region 220.

The heel region 330 includes rearfoot medial 340 and lateral 345 wedges. The rearfoot medial 340 and lateral 345 wedges intersect at an expected contact location of a medial side 125 of a midline of a heel 350 of the human foot on the heel region 330 of the orthotic device 300. An expected range arrow 375 indicates a range of possible intersections of the medial 340 and the lateral 345 wedges in the rearfoot (heel) region 330.

The medial wedge 340 in at least one of the toe 310, forefoot 315, midfoot 220, or heel 330 regions may have a larger or smaller angle than the lateral wedge 345 in the same region. In certain embodiments, the medial wedge 340 in the heel 330, midfoot 220, forefoot 315 and toe 310 regions have larger angles than the lateral wedge 345 in the same region. In at least one region, the medial wedge 340 may have a smaller angle than the lateral wedge 345 in that region.

The medial 340 and lateral 345 wedges may increase or decrease toward their respective intersection.

The medial wedge 340 (also referred to as a valgus wedge) extends from the heel region to the joint connecting the first metatarsal bone 240 and the medial cuneiform bone 250. The lateral wedge 345 (also referred to as a varus wedge) extends from the heel region to the midfoot and forefoot and into the toe area. The medial 340 and lateral 345 wedges are both extended into the forefoot and toe areas.

The medial wedge 340 is defined as a function of angles α and β, where angle α is defined as the angle in the vertical z-direction (where for purposes herein the term direction may refer to an axis of dimension) between the second 342 through the fifth 348 metatarsal heads relative to the heel, and angle β is defined as the angle in the vertical z-direction between the first 341 through the fifth 348 metatarsal heads relative to the heel. The measurements of angles α and β are usually obtained with the patient in a neutral subtalar joint position, loaded (closed chain) or simulating a loaded position.

The medial wedge 340 is carried beyond the metatarsal head and neck areas 341, 342, 344, 346, and 348 into the toe area. Together, the medial 340 and lateral 345 wedges allow for a gradual deceleration (pronation) starting at heel strike or foot contact to midstance and gradual acceleration (supination) from midstance to toe off and into the swing phase of gait. The wedges promote neutral function around the subtalar joint (rearfoot region), midtarsal joints (midfoot region), metatarsals (forefoot region), and toes (toe region).

By extending the medial wedge 340 under the first metatarsal head and neck 341 and the first toe 290, example embodiments of the present invention help maintain the foot on the orthotic. Therefore, the foot cannot move medially or laterally away from the orthotic. Additionally, the medial wedge 340 maintains the first metatarsal head and neck 341 in an anatomically neutral position relative to the midfoot 220 and rearfoot region 230 (FIG. 2) and the second metatarsal head and neck area 342.

Figure 5:
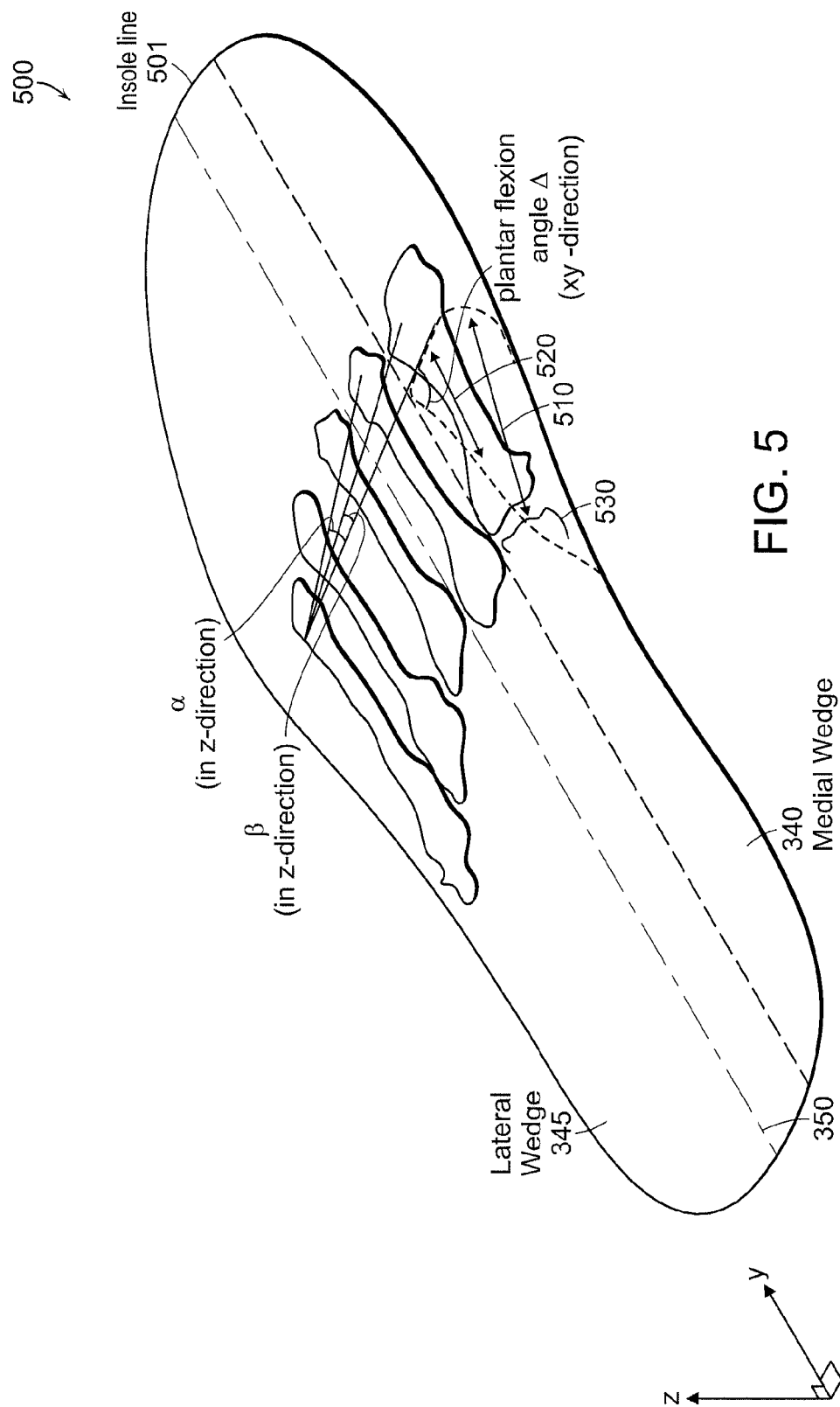
FIG. 5 is a diagram of an example embodiment of the present invention, including medial and lateral wedges as well as a plantar-flexion angle based support, in connection with a human foot.

FIG. 5 is a high level illustration of an example embodiment of the present invention that includes medial 340 and lateral wedges 345 as well as a plantar-flexion angle based support 520. The plantar-flexion angle based support 520 is defined by a contour of the medial wedge 340 and extends from an intersection of the medial wedge 340 and lateral wedge 345 at an expected contact location of a second metatarsal head and neck area 242 to, inclusively, between fore 520 and aft 530 joints of the first metatarsal bone 240 (and possibly slightly beyond) at an angle determined as a function of a degree of plantar-flexion of the first metatarsal bone 240. This angle is referred to as plantar flexion angle, sometimes as a "cutback" angle, and defined as a function of a difference between angles in a z-direction of first 341 and fifth 348 and second 342 and fifth 348 metatarsal heads.

Specifically, as explained in reference to FIG. 3, the medial wedge 340 is defined as a function of angles α and β, where angle α is defined as a function of the angle between the second 342 through the fifth 348 metatarsal heads relative to the heel and angle β is defined as a function of the angle between the first 341 through the fifth 348 metatarsal heads relative to the heel. The measurements of angles α and β are usually obtained with the patient in a neutral subtalar joint position, a loaded (closed chain) or simulating a loaded position. The plantar-flexion angle based support is defined using the plantar flexion angle Δ and may be determined as $$\Delta = \frac{\alpha - \beta}{A(\alpha - \beta) + B} * C$$

where A is a predetermined scaling factor, B is a predetermined offset, and C is a predetermined gain. The range 520 of the plantar-flexion angle-based support is shown in FIG. 5.

The plantar-flexion angle-based support may be extended beyond the metatarsal heads into the toe area to allow the foot to maintain a neutral position to toe off and into and through a swing phase. The plantar-flexion angle based support also maintains the metatarsal heads (specifically the first metatarsal head 341) in an anatomically ideal position relative to the rear foot region and the other metatarsals.

As explained above, the plantar-flexion angle Δ is determined as a function of measurements of angles α (second to fifth metatarsal angle) and β (first to fifth metatarsal angle). The first metatarsal bone 240 is generally a long bone that can range from two to more than four inches in length. The first metatarsal bone 240 is attached to the medial cuneiform bone 250, forming a joint 530 that moves up and down during dorsi-flexion and plantar-flexion movements.

A person with a first metatarsal bone that is highly plantar-flexed (whether a flat or high arched foot)) has a larger plantar-flexion angle Δ than the general population. Therefore, such a patient is likely to be prescribed an orthotic with a plantar-flexion angle based support that is relatively lesser than other persons (the support becomes smaller when there is a large plantar flexion angle delta). The plantar-flexion angle-based support maintains the forefoot to rearfoot relationship in midstance to toe off, controls pronation into midstance, and supination (or resupination) to toe off while controlling the amount of plantar flexion of the first metatarsal relative to the second through fifth metatarsals and the rearfoot, which maximizes the efficiency of the peroneus longus muscle and tendon. By controlling the amount of plantar flexion in conjunction with maintenance of the remaining metatarsal bones and the rearfoot region, the plantar-flexion angle-based support maximizes the function of muscles and tendons that maintain the stability of the first metatarsal bone and its fore and aft joints throughout the stance phase of gait and into the swing phase.

In order to maintain the stability of the fore and aft joints of the first metatarsal bone, the plantar-flexion angle based support maintains the rearfoot, midfoot, forefoot and toe regions in neutral positions throughout the stance phase into the swing phase of gait.

The medial 340 and lateral 345 wedges are arranged to dynamically control the motion of the human foot around the neutral positions as well as optimize the neutral position of the first metatarsal. The orthotic device 500 performs these functions in the rearfoot, midfoot, forefoot and toe regions of the foot throughout an entire gait cycle.

Figure 6A:
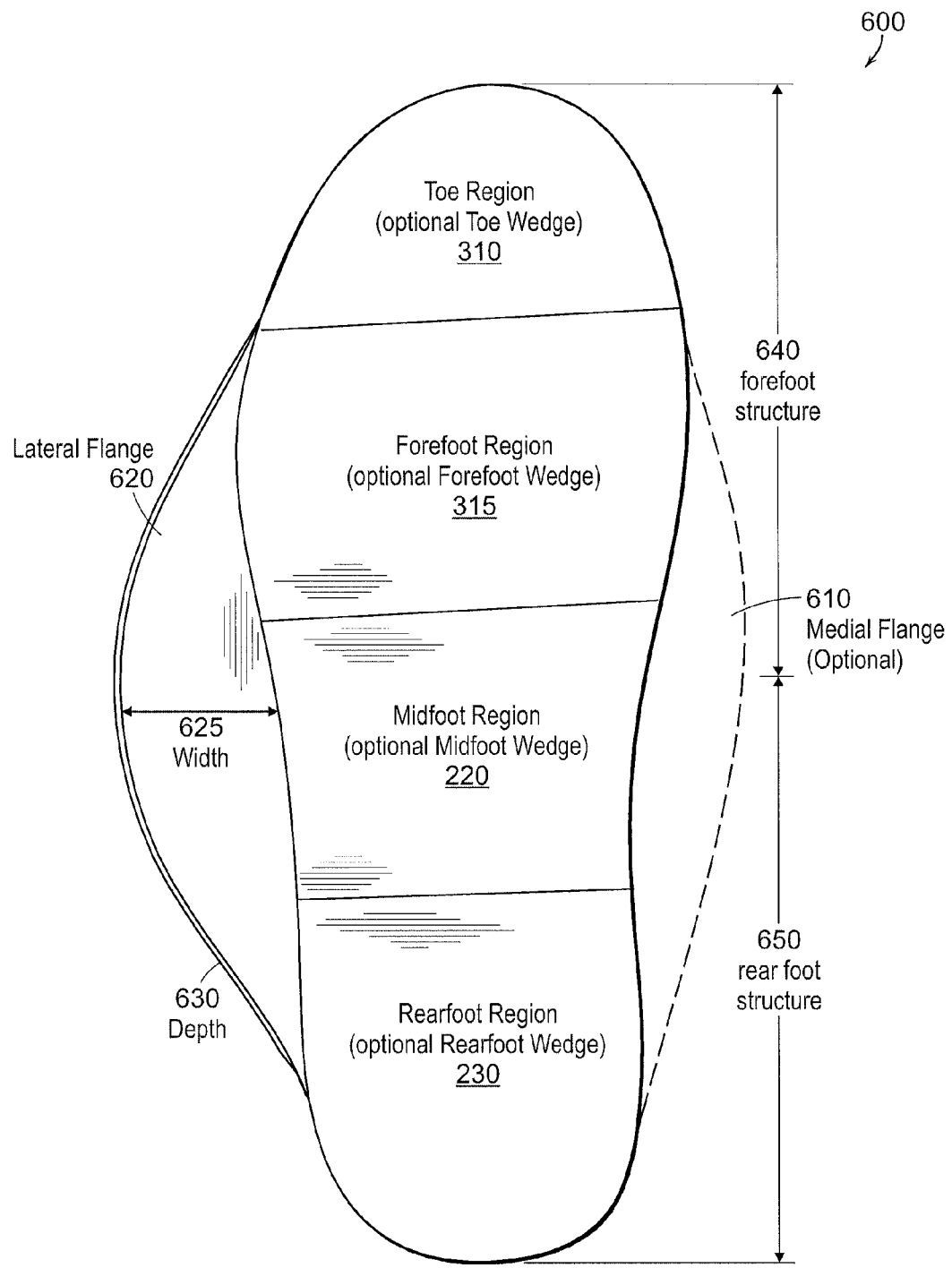
FIG. 6A is a schematic diagram of an example embodiment of the present invention, including medial and lateral flanges, in connection with a human foot.

FIG. 6A is a high level illustration of an example embodiment of an orthotic device 600 that includes medial 610 and lateral 620 flanges. The orthotic device 600 includes a forefoot structure 640, which includes a forefoot angle in the z direction, and a rearfoot structure 650, which includes a rearfoot angle in the z-direction. The forefoot structure 640 may include a toe region 310 with an optional toe wedge and a forefoot region 315 with an optional forefoot wedge. The rearfoot structure 650 includes a midfoot region 220 with an optional midfoot wedge and a rearfoot region 230 with an optional rearfoot wedge. The orthotic device 600 further includes a lateral flange 620 having a width, depth and length. The width 625, depth 630, and length 628 of the lateral flange 620 are defined as a function of the forefoot angle, rearfoot angle, or combination thereof. Specifically, an increase in the width of the forefoot structure or the rearfoot structure may result in an increase in the width 625, length 628 and/or depth 630 of the lateral flange 620.

The orthotic device 600 may further include an optional medial flange 610. The width of the medial flange 610 is defined as a function of the width of the foot. The lateral flange 620 prevents the foot from sliding laterally off the orthotic. If the forefoot 315 and midfoot 220 regions are highly angled (when forefoot angles and alpha and beta are high or the rearfoot angle is high) the forces asserted by these regions may cause the foot to slide off the orthotic within the shoe in which the orthotic is employed. This phenomenon may be compounded by the internal and external motion of the pelvis which can often significantly increase the lateral forces on the foot in these foot types. In order to overcome these issues, the lateral flange is changed based on the angle of the wedges and increased/decreased in width, length, and depth as rearfoot and forefoot angles increase/decrease.

Figure 6B:
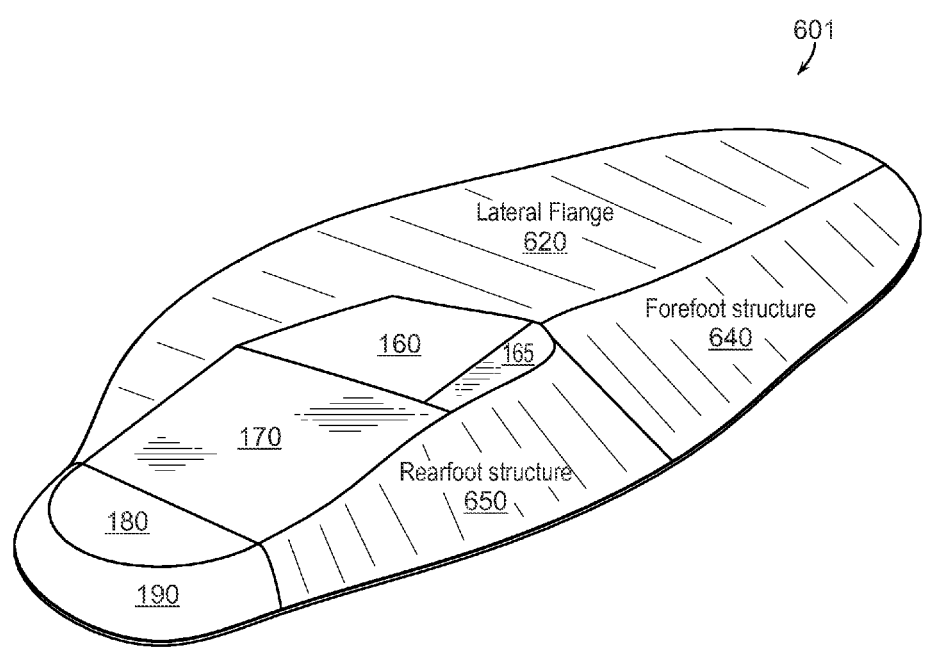
FIG. 6B is a mechanical diagram of an example embodiment of the present invention that includes a lateral flange.

FIG. 6B is a high level illustration of an orthotic device 601 according to an example embodiment of the present invention. The orthotic device 601 includes a forefoot structure 640, a rearfoot structure 650, and a lateral flange 620. The orthotic device may also include a rearfoot structure 180 as well as a heel wedge 190. The example embodiment may include multiple other structures 160, 165, and 170 designed to support the midfoot and rearfoot regions. Certain embodiments may create a series of wedges (e.g., wedges 180, 170, 160, 165) that extend from the heel to the midfoot and forefoot regions of the foot, beyond the metatarsal head and neck areas, into and through the toe area.

Figure 6C:
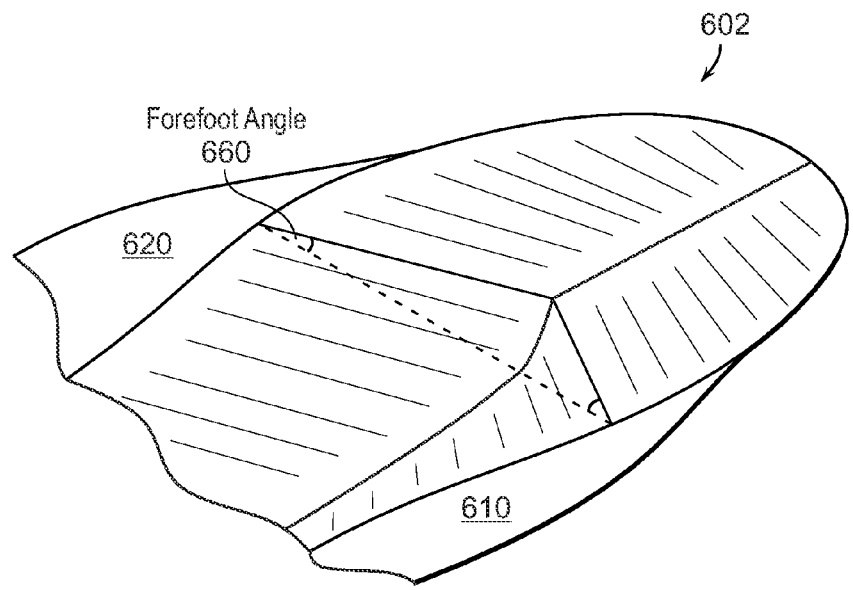
FIG. 6C is a diagram of an example of a forefoot angle that may be used in connection with example embodiments of the present invention.

FIG. 6C is an example of a forefoot angle that may be used in connection with example embodiments of the present invention. As explained in relation to FIG. 6A, the orthotic device 600 includes a forefoot structure 640 that includes a forefoot angle 660 as illustrated in the partial view of example orthotic device 602 shown in FIG. 6C.

Figure 6D:
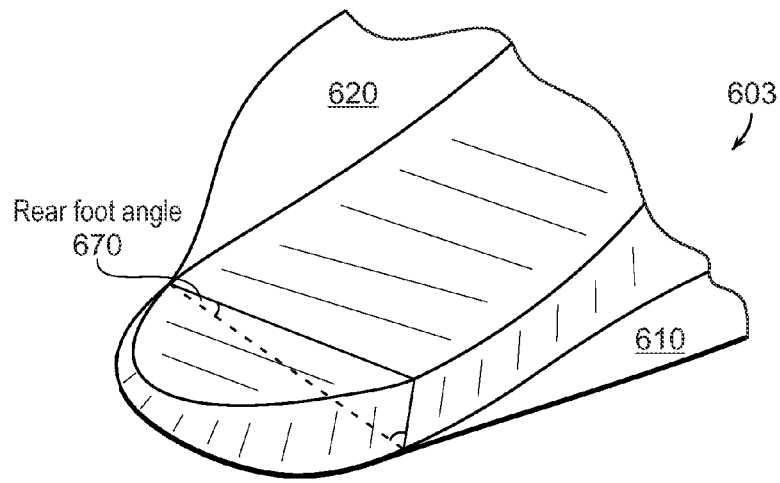
FIG. 6D is a diagram of an example of a rearfoot angle that may be used in connection with example embodiments of the present invention.

FIG. 6D is an example of a rearfoot angle that may be used in connection with example embodiments of the present invention. As explained in relation to FIG. 6A, the orthotic device 600 may include a rearfoot structure 650 that includes a rearfoot angle 670 as illustrated in the partial view of example orthotic device 603 shown in FIG. 6D.

Figure 7:
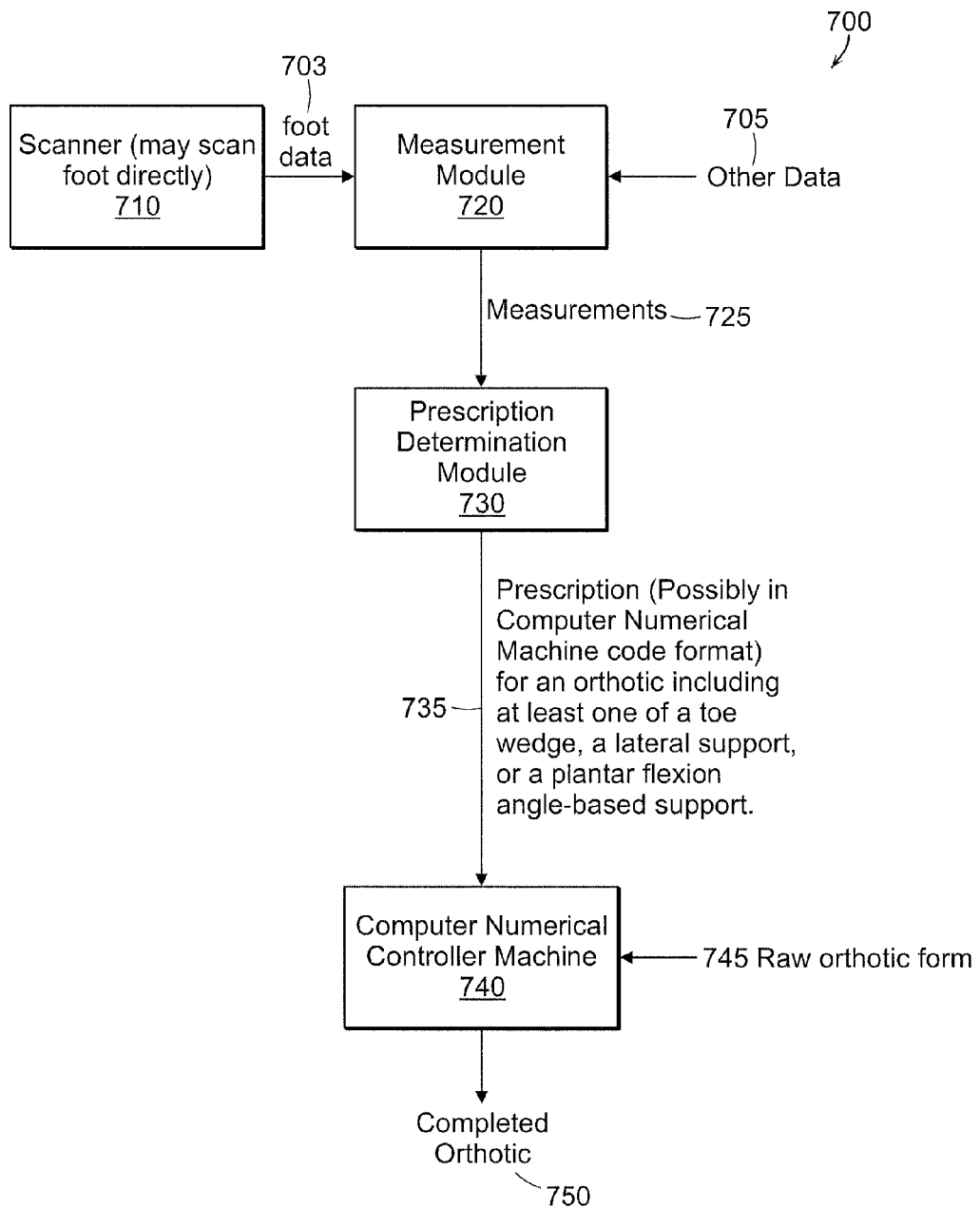
FIG. 7 is a flow diagram of an example method for enabling a computer numerically controlled (CNC) machine to produce an orthotic device corresponding to an embodiment of an orthotic device of the present invention.

FIG. 7 is a flow diagram 700 of procedures for enabling a computer numerically controlled (CNC) machine to produce an orthotic device according to embodiments of the present invention. The example embodiment may include a scanner 710 that scans the foot directly to determine foot data 703. The example embodiment includes a measurement module 720 that obtains measurements of width and length of a human foot (e.g., biomechanical measurements) and determines locations of metatarsal heads of the human foot. The location of metatarsal heads may possibly be obtained using the foot data 703 obtained from the scanner 710 or other data 705 obtained from other data sources (not shown), including, for example, hand or observed measurement taken during podiatrist or orthopedic examination obtained from other data sources. The measurement module 720 forwards the measurements 725, in raw or processed format, to a prescription determination module 730. The prescription determination module 730 determines the prescription 735 for an orthotic device, including a toe wedge, plantar flexion angle-based support, or lateral flange based on measurements and locations of the metatarsal heads, as described above. The example embodiment may forward the determined prescription 735 to a computer numerically controlled (CNC) machine 740. The CNC machine 740 may produce the orthotic device 750 from raw material 745 according to the prescription 735.

Figure 8:
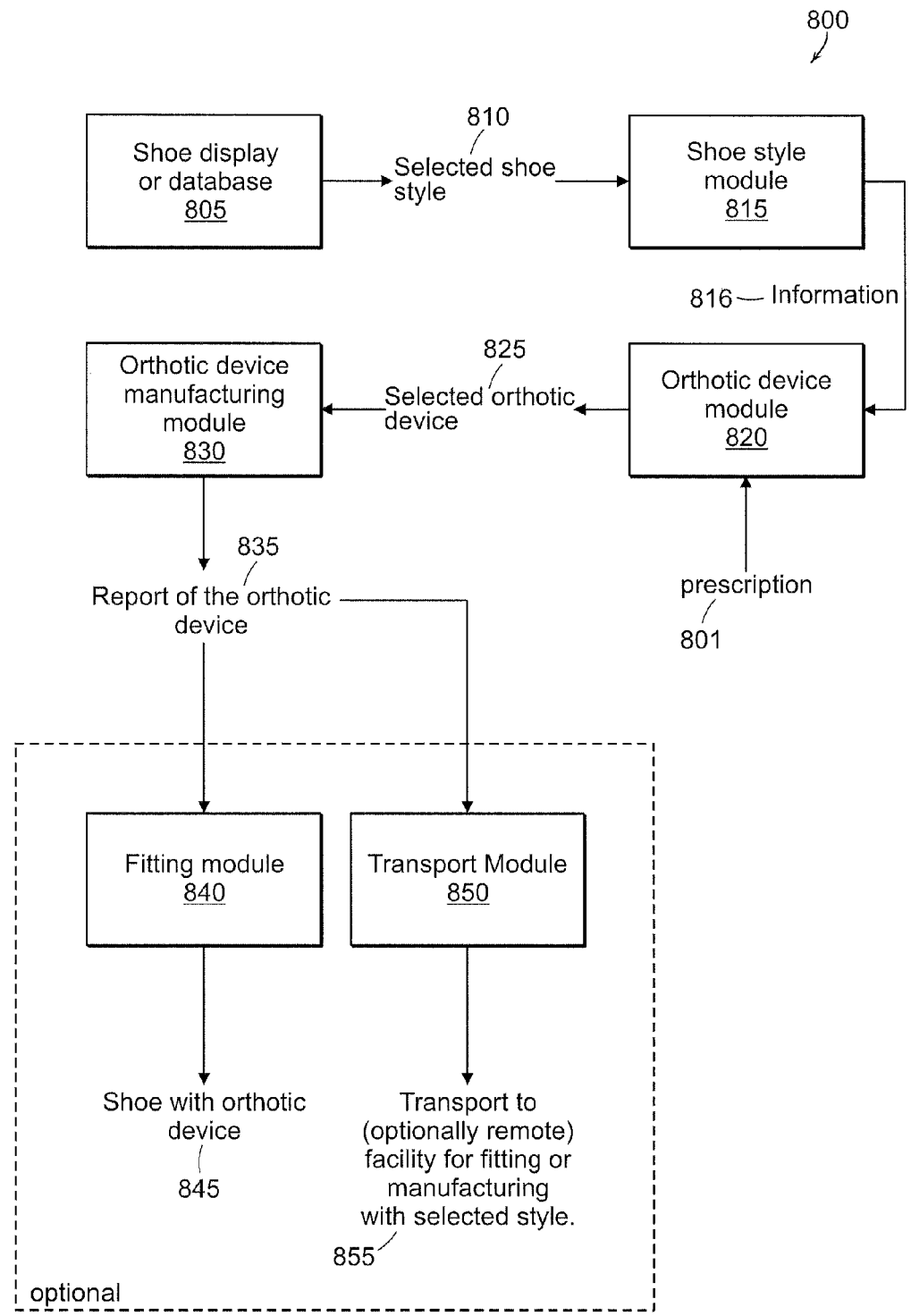
FIG. 8 is a high level flow diagram of procedures for manufacturing an orthotic device according to an embodiment of the present invention.

FIG. 8 is a high level flow diagram 800 of procedures for manufacturing an orthotic device according to an example embodiment of the present invention. The example embodiment may obtain a selected shoe style 810 by utilizing a shoe display or database 805 from which a patient can select a shoe style 810. A shoe style module 815 receives the desired/selected shoe style 810 and forwards the information 816 regarding the shoe style to an orthotic device module 820. The orthotic device module 820 selects an orthotic device configured to be used with the desired shoe style. The orthotic device includes a toe wedge, plantar flexion angle-based support, or lateral flange, as described above, and is configured based on a prescription 801 of an orthotic device specified to arrange metatarsal heads of the patient's feet in a functionally corrected anatomical position from heel strike through toe off.

An orthotic device manufacturing module 830 utilizes information regarding structure of the selected orthotic device 825 to produce an orthotic device or to produce a report 835 regarding the selected orthotic device 825. The report 835 or information therein may be transferred by a transport module 850 to a facility that manufactures or fits the orthotic device with the selected shoe style 855. Alternatively, a fitting module may fit the manufactured orthotic device in the selected shoe style and provide the patient with the shoe including the orthotic 845.

Figure 9:
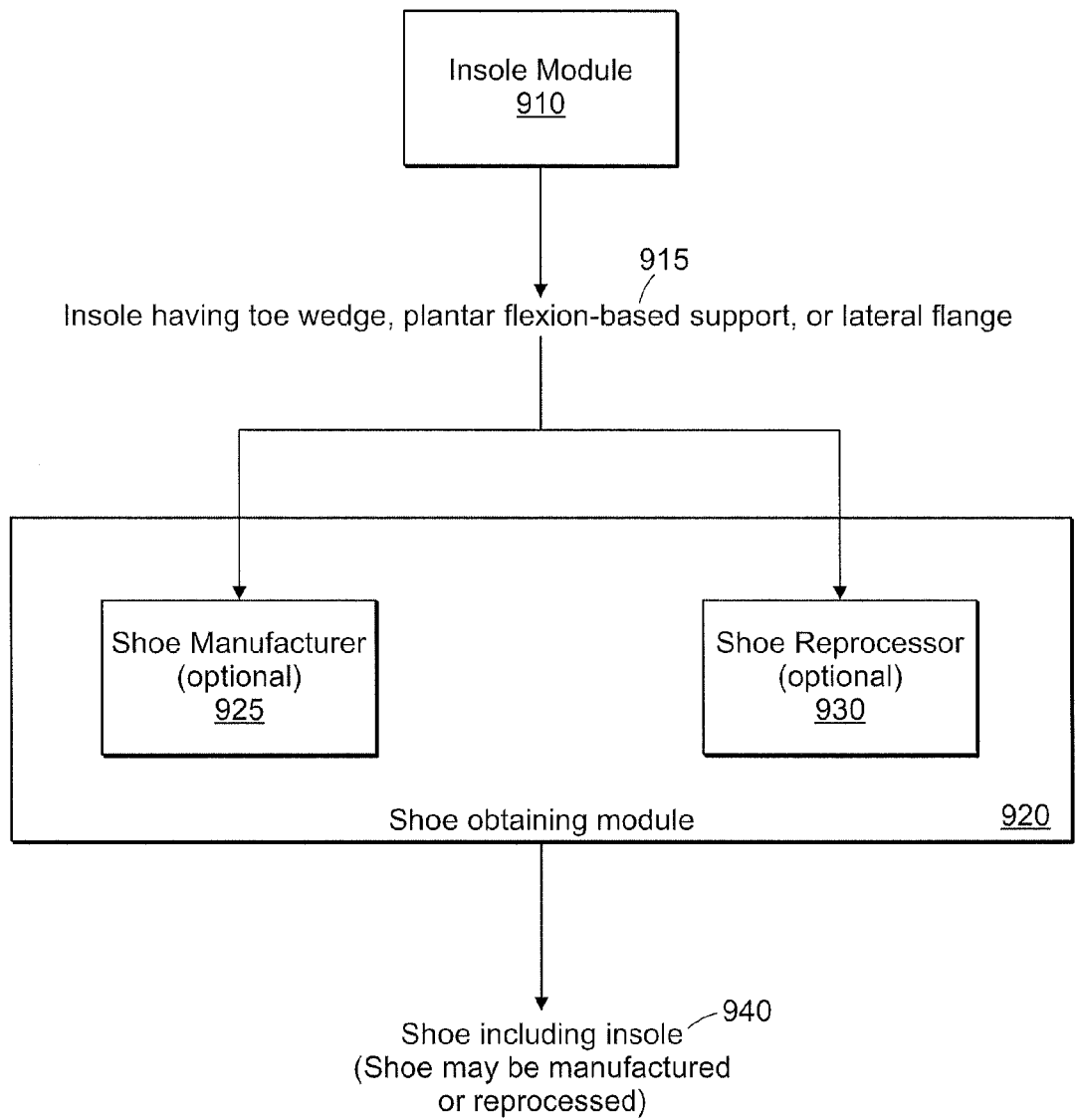
FIG. 9 is a flow diagram of an example method for transforming a shoe to improve anatomical position of a wearer's feet from heel strike to toe off using embodiments of the present invention.

FIG. 9 is a flow diagram 900 of an example of procedures for transforming a shoe to improve anatomical position of a wearer's foot from heel strike through toe off using embodiments of the present invention. The example procedure employs an insole module 910 that provides an insole having a toe wedge, plantar flexion angle-based support, or lateral flange 915. The example procedure further includes a shoe obtaining module 920 that obtains a shoe. The shoe obtaining module 920 may obtain the shoe by manufacturing the shoe 925 and employing the insole by shaping the sole of the shoe to accommodate the insole. The shoe obtaining module 920 may alternatively obtain the shoe from a shoe re-processor 930, which fits the insole in a reprocessed shoe. The shoe obtaining module 920 produces a shoe (manufactured or reprocessed) including an insole 940.

Figure 10:
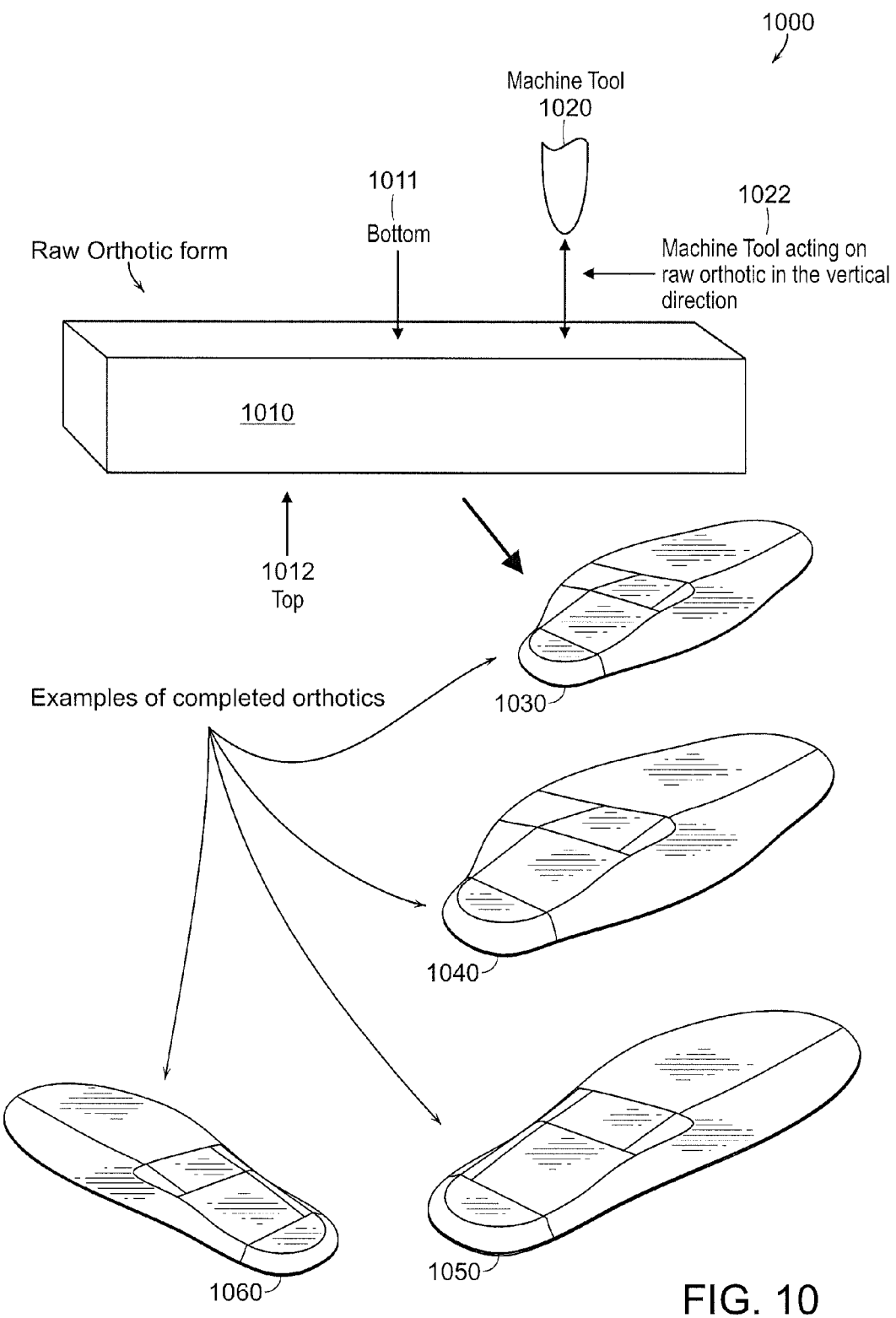
FIG. 10 is a high level procedure involved in manufacturing an orthotic device according to example embodiments of the present invention.

FIG. 10 illustrates an embodiment of high level procedures 1000 involved in manufacturing an orthotic device according to example embodiments of the present invention. The example embodiment may employ a machine tool 1020 that acts on raw orthotic material 1010 in a vertical direction 1022 (i.e., perpendicular to a planar surface (i.e., top or bottom) of the orthotic device). Example embodiments of the present invention may mill the raw orthotic material from a top surface 1012 of the raw orthotic 1010 and along a vertical axis 1022 of the raw orthotic 1010. Certain embodiments of the present invention may mill the raw orthotic material from a bottom portion 1011 of the raw orthotic 1010 and along a vertical axis 1022 of the raw orthotic 1010. An advantage of milling the orthotic device from the bottom side of the orthotic device is that the produced orthotic device has a smooth top surface that interfaces with the patient's foot, leading to a more comfortable experience for the patient in addition to the structural improvements imparted to the patient's feet, ankles, legs, hips, and back. Some examples of completed orthotics 1030, 1040, 1050, 1060 are illustrated in FIG. 10.

Figure 11:
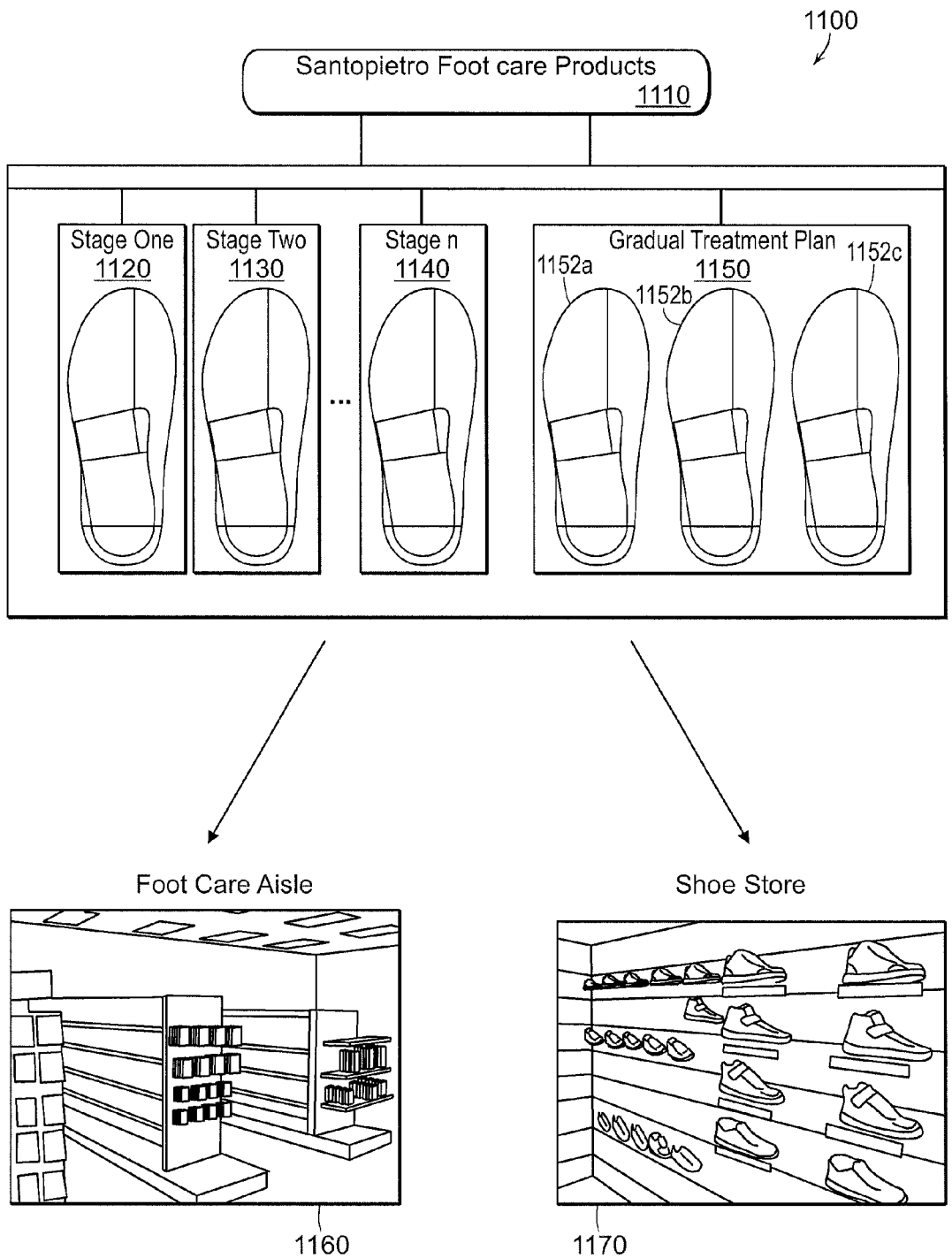
FIG. 11 is a diagram of a multi-level orthotic device kit made available at a retail location.

FIG. 11 is a high level illustration 1100 of a multi-level orthotic device kit 1150 for controlling a person's foot. The multi-level orthotic device kit 1150 includes multiple orthotic devices 1152-a, 1152-b, . . . , 1152-c including a first level orthotic device 1152-a, final level orthotic device 1150-c, and intermediate level orthotic device(s) 1152-b. The multiple orthotic devices are arranged to facilitate transitioning the human foot from wearing the first level orthotic device 1152-a to the final level orthotic device 1152-c over a given length of time. The final level orthotic device 1152-c corresponds to a prescription for the person determined to support the person's foot in a functionally corrected anatomical position using at least one of a toe wedge, plantar flexion angle-based support, or lateral flange. The multi-level kit 1150 may be distributed in a physician's office (not shown), shoe store 1170, and/or at a foot care aisle 1160 of a drug store (displayed in FIG. 11 as "Santopietro Foot Care Products" 1110). Alternatively, the individual elements 1120, 1130, 1140 of a multi-level kit may be made available for individual sale.

It should be understood that procedures, such as those illustrated by flow diagram or block diagram herein or otherwise described herein, may be implemented in the form of hardware, firmware, or software. If implemented in software, the software may be implemented in any software language consistent with the teachings herein and may be stored on any computer readable medium known or later developed in the art. The software, typically, in form of instructions, can be coded and executed by a processor in a manner understood in the art.

While this invention has been particularly shown and described with references to example embodiments thereof, it will be understood by those skilled in the art that various changes in form and details may be made therein without departing from the scope of the invention encompassed by the appended claims.

What is claimed is:

1. An orthotic device for controlling motion of a human foot in a functionally corrected anatomical position from heel strike through toe off, the orthotic device comprising:
    a rearfoot region including rearfoot medial and lateral wedges, the rearfoot medial and lateral wedges intersecting at an expected contact location of a medial side of a midline of a heel of the human foot on the rearfoot region of the orthotic device;
    a midfoot region including midfoot medial and lateral wedges, the midfoot medial and lateral wedges intersecting inclusively between expected contact locations of a first cuneiform bone and a cuboid bone on the midfoot region of the orthotic device;
    a forefoot region including forefoot medial and lateral wedges, the forefoot medial and lateral wedges intersecting inclusively between expected contact locations of first and fifth metatarsal bones on the forefoot region of the orthotic device;
    a toe region including toe medial and lateral wedges, the toe medial and lateral wedges intersecting inclusively between expected contact locations of first and fifth toes on the toe region of the orthotic device; and
    a support, defined by a contour of the forefoot medial wedge, extending from an intersection of the forefoot medial wedge and forefoot lateral wedge beginning at an expected contact location of a second metatarsal head and neck area, the support projecting inclusively between fore and aft joints of the first metatarsal bone at an angle determined as a function of a degree of plantar-flexion of the first metatarsal bone, the angle referred to as a plantar flexion angle and defined as a function of a difference between angles in a z-direction of first and fifth and second and fifth metatarsal heads,
    the medial and lateral wedges being defined in a coronal plane, the medial and lateral wedges having corresponding medial and lateral angles greater than zero in the coronal plane, the medial and lateral wedges having corresponding edges distal from the respective intersections and wherein the wedges increase in height from their edges toward the respective intersections.

2. The orthotic device of claim 1 wherein at least one of the medial wedges has a larger angle than its corresponding lateral wedge.

3. The orthotic device of claim 1 wherein at least one of the medial wedges has a smaller angle than its corresponding lateral wedge.

4. The orthotic device of claim 1 wherein the medial wedges in the rearfoot, midfoot, and forefoot regions have larger angles than their respective lateral wedges and wherein the medial wedge in the toe region has a smaller angle than its corresponding lateral wedge.

5. The orthotic device of claim 1 wherein the medial and lateral wedges constitute a heel-to-toe wedge, the heel-to-toe wedge increasing or decreasing in height from the rearfoot region to the forefoot region.

6. The orthotic device of claim 1 wherein the respective intersections of the medial and lateral wedges form a continuous intersection extending from the rearfoot region to the toe region.

7. The orthotic device of claim 1, wherein the medial and lateral wedges are visible in an uncompressed state.

8. The orthotic device of claim 1, further comprising:
    a lateral flange having a width and depth, the width and depth being a function of an angle of at least one of the lateral wedges in the toe region or forefoot region in the coronal plane, an angle of at least one of the lateral wedges in the midfoot region or rearfoot region in the coronal plane, or combination thereof.

9. An orthotic device for controlling motion of a human foot in a functionally corrected anatomical position, the orthotic device comprising:
    a medial wedge;
    a lateral wedge;
    an intersection defined where the medial and lateral wedges intersect, the intersection extending from a medial side of a midline of a heel of the human foot to, and inclusively between, expected contact locations of first and fifth toes of the foot on the orthotic device, the medial wedge, lateral wedge, and intersection configured to support the human foot in a functionally corrected anatomical position from heel strike through toe off, the medial and lateral wedges being defined in a coronal plane, the medial and lateral wedges having corresponding medial and lateral angles greater than zero in the coronal plane, the medial and lateral wedges having corresponding edges distal from the intersection and wherein the wedges increase in height from their edges toward the intersection; and
    a support, defined by a contour of the medial wedge, extending from an intersection of the medial wedge and lateral wedge beginning at an expected contact location of a second metatarsal head and neck area, the support projecting inclusively between fore and aft joints of a first metatarsal bone at an angle determined as a function of a degree of plantar-flexion of the first metatarsal bone, the angle referred to as a plantar flexion angle and defined as a function of a difference between angles in a z-direction of first and fifth and second and fifth metatarsal heads.

10. The orthotic device of claim 9 wherein the medial wedge is defined by an angle greater than the lateral wedge for a length of at least a portion of the orthotic device.

11. The orthotic device of claim 9 wherein the medial wedge is defined by an angle less than the lateral wedge for a length of at least a portion of the orthotic device.

12. The orthotic device of claim 9, wherein the medial and lateral wedges are visible in an uncompressed state.

13. The orthotic device of claim 9, further comprising:
    a forefoot structure having a forefoot angle of the lateral wedge in the coronal plane;

a rearfoot structure having a rearfoot angle of the lateral wedge in the coronal plane; and
a lateral flange having a width and depth, the width and depth being a function of the forefoot angle of the lateral wedge in the coronal plane, rearfoot angle of the lateral wedge in the coronal plane, or combination thereof.

* * * * *